US009518959B2

United States Patent
Malladi et al.

(10) Patent No.: US 9,518,959 B2
(45) Date of Patent: Dec. 13, 2016

(54) STRUCTURAL HEALTH MONITORING SYSTEM AND METHOD

(71) Applicant: Texas Instruments Incorporated, Dallas, TX (US)

(72) Inventors: Rakesh Malladi, Houston, TX (US); Anand G. Dabak, Plano, TX (US); Nitish Krishna Murthy, Allen, TX (US)

(73) Assignee: TEXAS INSTRUMENTS INCORPORATED, Dallas, TX (US)

(*) Notice: Subject to any disclaimer, the term of this patent is extended or adjusted under 35 U.S.C. 154(b) by 183 days.

(21) Appl. No.: 14/458,036

(22) Filed: Aug. 12, 2014

(65) Prior Publication Data

US 2015/0040671 A1 Feb. 12, 2015

Related U.S. Application Data

(60) Provisional application No. 61/864,906, filed on Aug. 12, 2013.

(51) Int. Cl.
*G01N 29/04* (2006.01)

(52) U.S. Cl.
CPC ... *G01N 29/041* (2013.01); *G01N 2291/02854* (2013.01)

(58) Field of Classification Search
CPC ............... G01N 29/041; G01N 2291/02854
USPC ................................................. 73/655, 597
See application file for complete search history.

(56) References Cited

U.S. PATENT DOCUMENTS

| | | | | |
|---|---|---|---|---|
| 5,438,872 A | * | 8/1995 | Kobayashi | G01B 17/02 73/12.01 |
| 5,570,302 A | * | 10/1996 | Kobayashi | G06F 3/0433 178/18.04 |
| 5,965,818 A | * | 10/1999 | Wang | G01B 17/02 73/598 |
| 5,996,415 A | * | 12/1999 | Stanke | G01N 29/041 374/119 |
| 2004/0105101 A1 | * | 6/2004 | Shinya | G01B 11/0675 356/630 |

* cited by examiner

*Primary Examiner* — J M Saint Surin
(74) *Attorney, Agent, or Firm* — John R. Pessetto; Charles A. Brill; Frank D. Cimino

(57) ABSTRACT

A method includes: transmitting, via a signal generator, an electrical driving signal, the electrical driving signal having a mean square error; transmitting, via a wave generating component, a Lamb wave, the Lamb wave having many different modes; estimating, via an estimating component, a propagation parameter associated with the Lamb wave; and estimating, via an estimating component, a thickness of a material.

20 Claims, 9 Drawing Sheets

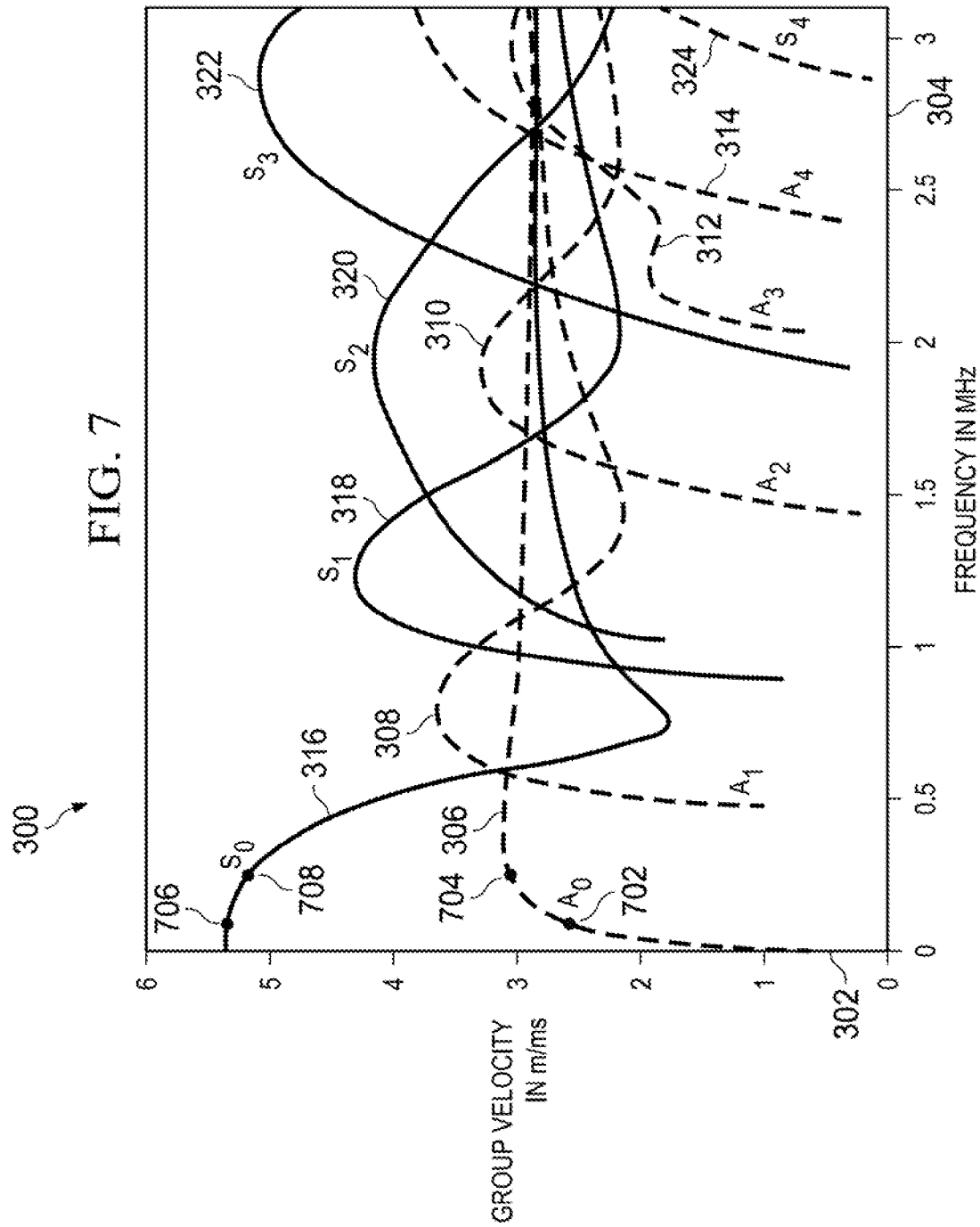

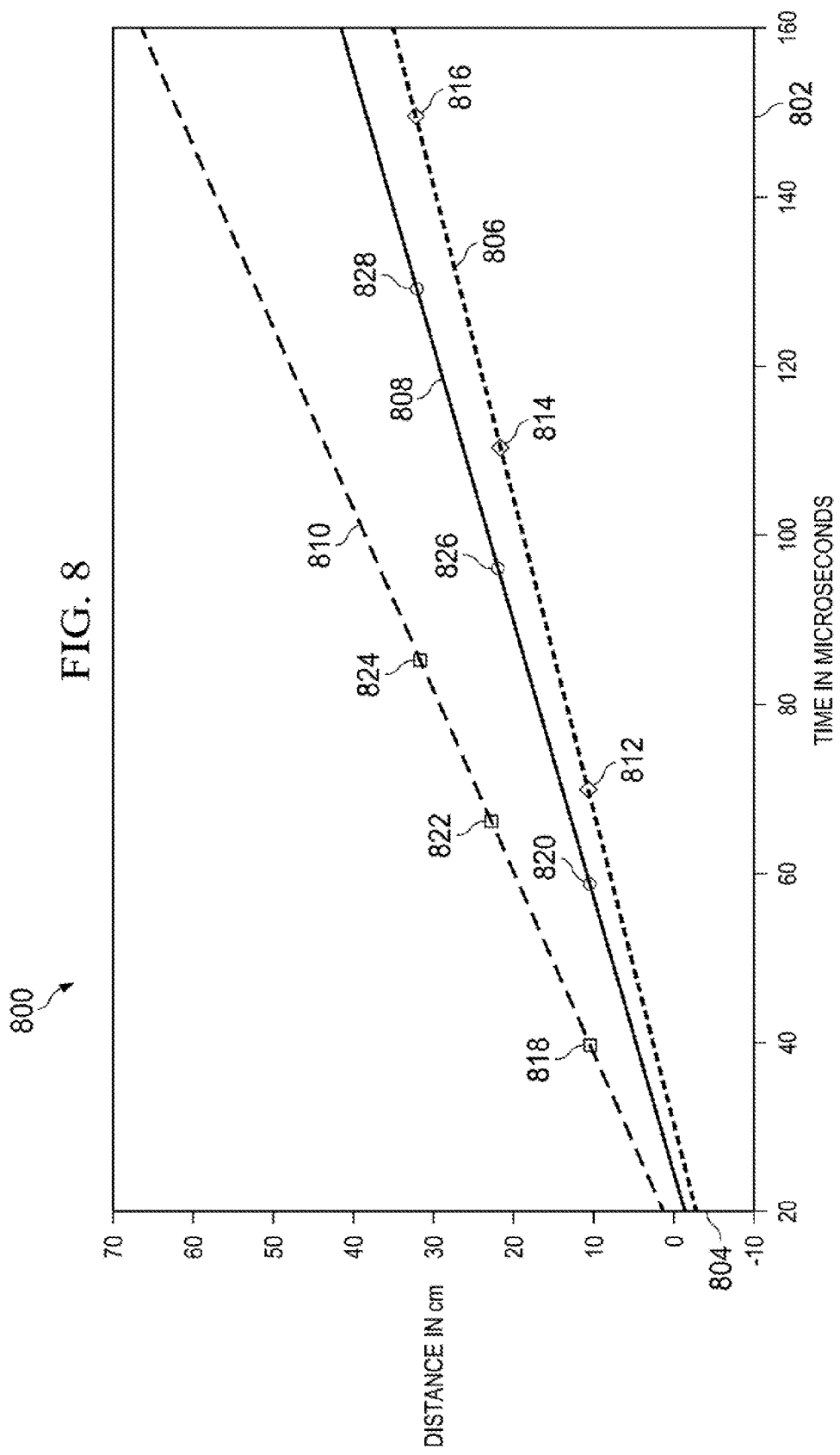

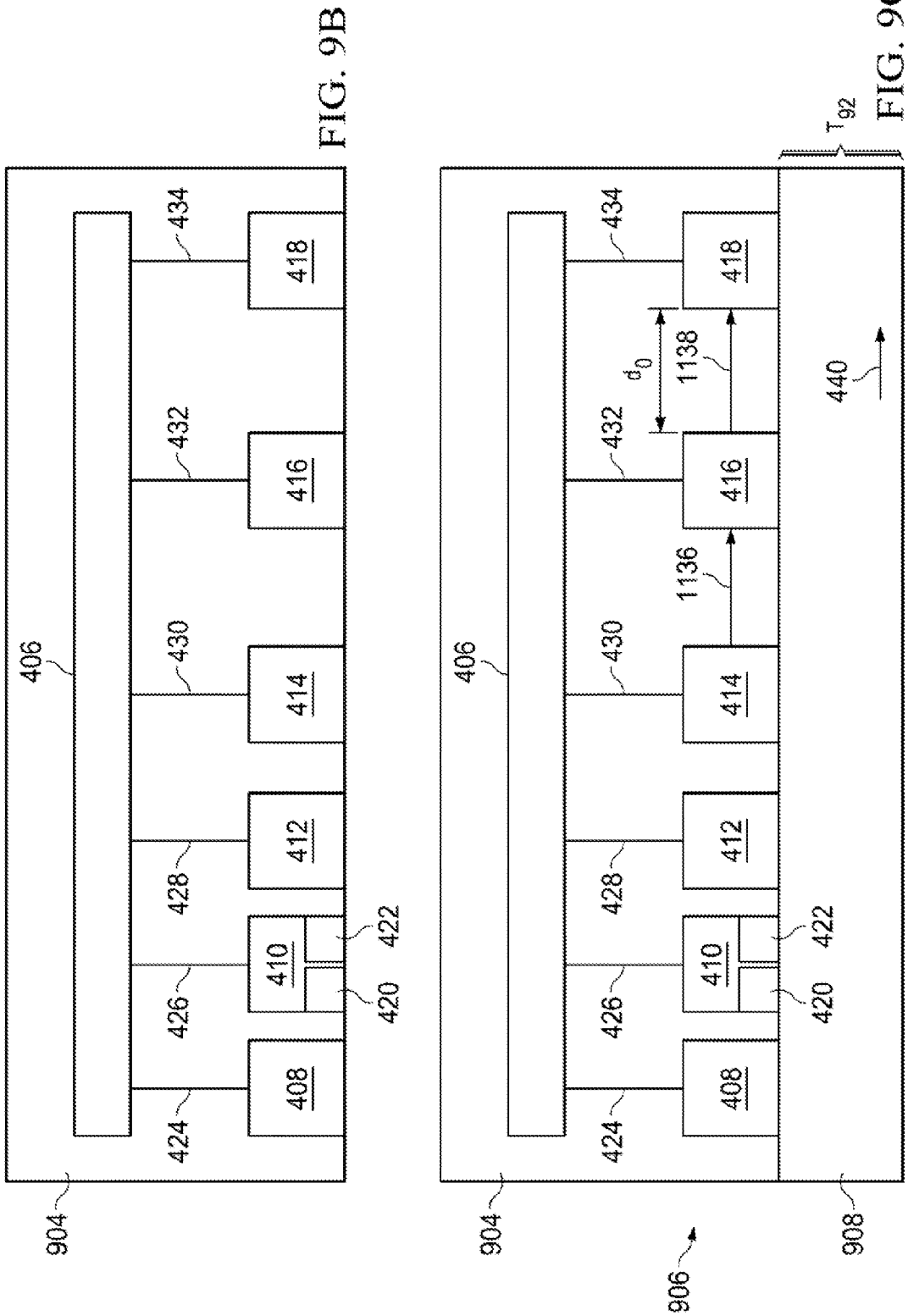

STRUCTURAL HEALTH MONITORING SYSTEM AND METHOD

The present application claims priority from: U.S. Provisional Application No. 61/864,906 filed Aug. 12, 2013, the entire disclosure of which is incorporated herein by reference.

BACKGROUND

Lamb waves are a type of wave that may be propagated though a material, in a manner similar to sound waves propagating though a fluid. The direction of vibration of a particle within the material, as the wave propagates, classifies the type of wave. In particular, if the particle vibrates in a direction that is parallel with the surface of the material and in a direction that is perpendicular with the wave propagation direction, then the wave is a shear-horizontal wave. If the particle vibrates in it direction that is normal with the surface of the material and in the wave propagation direction, then the wave is a Lamb wave. The different types of waves will now be described with reference to FIG. 1.

FIG. 1 illustrates propagation of waves through a material 100.

As shown in the figure, material 100 has a top surface 101, has a thickness, T, and is positioned about a y-axis 102, an x-axis 104, a z-axis 106. A particle 108 is disposed within material 100. A wave generating component 103 and a receiving component 105 are disposed on top surface 101 a distance, d, from one another. Also shown on the left side of the figure is a plane 110 about particle 108, wherein plane 110 includes a y-axis 112, x-axis 104 and a z-axis 114. In plane 110, particle 108 vibrates between a direction indicated by arrow 116 and a direction indicated by arrow 118 as a wave propagates in a direction indicated by arrow 120 in the case of a shear-horizontal wave, wherein plane 110 includes y-axis 112, x-axis 104 and z-axis 114. In this portion of the figure, in plane 110, particle 108 vibrates between a direction indicated by arrow 122 and a direction indicated by arrow 124 as a wave propagates in a direction indicated by arrow 120.

Wave generating component 103 generates a Lamb wave for receiving component 105. Wave generating component 103 may be any type of electromechanical transducer that is operable to convert electrical energy to mechanical energy, a non-limiting example of which includes a piezoelectric device. Receiving component 105 is operable to detect a wave propagated from wave generating component 103.

Suppose that a wave generating component 103 induces vibrations in material 100 at top surface 101 near the position of particle 108. If the vibrations are of a sufficient frequency, waves will propagate from the point of particle 108 in many directions. For purposes of discussion, consider the waves in the direction indicated by arrow 120 toward the end of material 100 indicated by plane 128 having particle 126 therein. The waves will be detected by receiving component 105. Of these waves, two types are shown in the figure. A shear-horizontal wave is illustrated with reference to the lower left of the figure, whereas a Lamb wave is illustrated in with reference to the lower right of the figure. For the purposes of discussion, consider only the lamb waves.

A shear-horizontal wave is distinguishable from a Lamb wave by the vibrational direction of the particles within the material as the wave propagates. As shown in the figure, in a shear-horizontal wave, particle 108 vibrates in a direction parallel with top surface 101 and perpendicular to the direction 120 of the wave propagation. On the other hand, in a Lamb wave, particle 108 vibrates in a direction perpendicular with top surface 101 and parallel to the direction 120 of the wave propagation.

The present application is generally drawn to the use of Lamb waves in detecting a thickness of a material.

There are two types of Lamb waves, anti-symmetrical and symmetrical. The differences will be discussed with reference to FIG. 2.

FIG. 2 illustrates a view of plane 128 of material 100 of FIG. 1.

As shown in FIG. 2, a particle 200 moves in a positive direction in y-axis 112 and in a positive direction of x-axis 104, whereas a particle 202 moves in a negative direction in y-axis 112 and in a positive direction of x-axis 104. This is an example of symmetrical motion, wherein the symmetry is about the middle of the plane. On the other hand, a particle 204 moves in a positive direction in y-axis 112 and in a positive direction of x-axis 104, whereas a particle 206 moves in a positive direction in y-axis 112 and in a negative direction of x-axis 104. This is an example of anti-symmetrical motion.

To further the discussion, it should be noted that some thicknesses of materials may support many different modes of each type of anti-symmetrical and symmetrical Lamb waves. This will be described in greater detail with reference to FIG. 1 and additional reference to FIG. 3.

Returning to FIG. 1, a Lamb wave propagating from wave generating component 103 to receiving component 105 will propagate the distance d. By measuring the time of propagation $t_p$, the velocity, V, of the Lamb wave may be calculated as:

$$V = d/t_p \qquad (1)$$

Different modes of Lamb waves have different velocities through a common material. This will be described in further detail with reference to FIG. 3.

FIG. 3 illustrates a graph 300 of measured frequency versus measured group velocity for different modes of Lamb waves propagated through a 3.18 mm thick aluminum plate.

As shown in the figure, graph 300 includes a y-axis 302, an x-axis 304, functions 306, 308, 310, 312 and 314 and functions 316, 318, 320, 322 and 324, Y-axis 302 is a group velocity of a mode of Lamb wave and is measured in m/ms. X-axis 304 is the frequency of the vibration within the Lamb wave and is measured in MHz.

Functions 306, 308, 310, 312 and 314 each represent the frequency of vibration within a Lamb wave as a function of the group velocity of the Lamb wave for anti-symmetric modes. Functions 316, 318, 320, 322 and 324 are the frequency of vibration within a Lamb wave as a function of the group velocity of the Lamb wave for symmetric modes.

Generally speaking, the velocity of a Lamb wave is a function of the thickness of the material though which it is propagating and the frequency. With reference to FIG. 3, even though all modes travel through the same material, i.e., the same thickness of material, the different modes travel at different velocities.

As the frequency of the vibration increases, the number of modes, which the frequency supports, increases. At low frequencies, only a few modes may be supported. For example, at about 0.25 MHz, only mode 306 and mode 316 are supported. On the other hand, at a frequency of 1.5 MHz, mode 306, mode 316, mode 308, mode 318, mode 310 and mode 320 are supported.

Structural health monitoring (SHM) is important for detecting changes in the thickness of a material over time.

Changes in thickness may be caused, for example, due to cracks or corrosion. If detected, cracks or corrosion, among other types of deterioration, may be treated by applying preventative maintenance to the material.

Conventionally, several methods have been used to monitor the structural health of a material. For example, ultrasonic transducers have been placed on the top and bottom surfaces of a material to detect changes in thickness of the material over time by analyzing ultrasonically generated Lamb waves.

However, it is difficult to place transducers in locations such that the transducer on the top surface of the material is precisely above the transducer on the bottom surface of the material. These offsets in positioning cause the thickness measurements from the ultrasonic waves to be inaccurate.

What is needed is a system and method which accurately conveys the thickness of a material. This system and method would be used to measure the thickness of a material at different points in time to determine the structural health of the material.

BRIEF SUMMARY

The present invention provides a system and method which uses the transmission of Lamb waves to accurately estimate the thickness of a material.

In accordance with aspects of the present invention, a method includes: transmitting, via a signal generator, an electrical driving signal, the electrical driving signal having a mean square error; transmitting, via a wave generating component, a Lamb wave, the Lamb wave having many different modes; estimating, via an estimating component, a propagation parameter associated with the Lamb wave; and estimating, via an estimating component, a thickness of a material.

Additional advantages and novel features of the invention are set forth in part in the description which follows, and in part will become apparent to those skilled in the art upon examination of the following or may be learned by practice of the invention. The advantages of the invention may be realized and attained by means of the instrumentalities and combinations particularly pointed out in the appended claims.

BRIEF SUMMARY OF THE DRAWINGS

The accompanying drawings, which are incorporated in and form a part of the specification, illustrate an exemplary embodiment of the present invention and, together with the description, serve to explain the principles of the invention. In the drawings:

FIG. 7 illustrates a graph of measured frequency versus measured group velocity for different modes of a Lamb wave;

FIG. 8 illustrates a graph of distance travelled versus time travelled for various Lamb waves; and FIGS. 9A-C illustrates an embodiment of a SHM system, in accordance with aspects of the present invention.

DETAILED DESCRIPTION

In accordance with aspects of the present invention, an initial thickness of a material to be measured is provided. A Lamb wave is propagated along the material. The Lamb is analyzed to estimate a first propagation parameter and a second propagation parameter. These estimated propagation parameters are then used to calculate a new estimated thickness of the material.

Aspects of the present invention will be described in greater detail with reference to FIGS. 4-9C.

A SHM system, in accordance with aspects of the present invention will now be described in more detail in FIG. 4.

Figure 4:
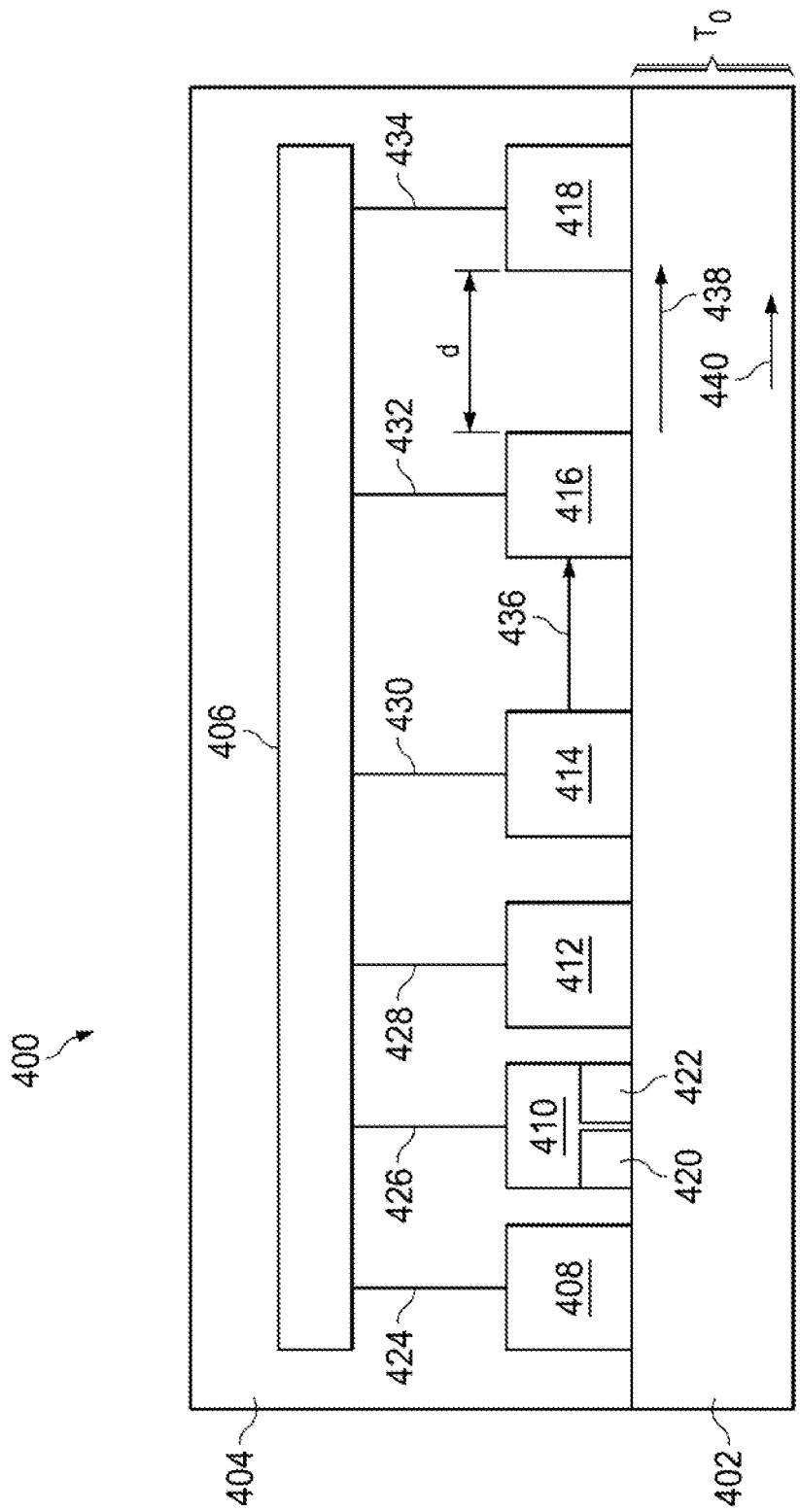
FIG. 4 illustrates an example system in accordance with aspects of the present invention.

FIG. 4 illustrates a device 400 in accordance with aspects of the present invention.

As shown in the figure, device 400 includes a material 402 and a monitoring portion 404. In some embodiments, material 402 and monitoring portion may be unitary. In other embodiments, monitoring portion 404 may be distinct and separable from material 402. For purposes of discussion, in the embodiment of FIG. 4, material 402 and monitoring portion 404 are unitary.

Monitoring portion 404 includes a controlling component 406, a memory component 408, a parameter estimating component: 410, a thickness estimating component 412, a signal generator 414, a wave generating component 416 and a receiving component 418. Parameter estimating component 410 includes a time estimating component 420 and an attenuation estimating component 422. Monitoring component additionally includes a control line 424, a control line 426, a control line 428, a control line 430, a control line 432 and a control line 434.

In this example embodiment, memory component 408, parameter estimating component 410, thickness estimating component 412, signal generator 414, wave generating component 416 and receiving component 418 are illustrated as independent components. However, in some embodiments, at least one of memory component 408, parameter estimating component 410, thickness estimating component 412, signal generator 414, wave generating component 416 and receiving component 418 may be implemented as a unitary component.

Memory component 408 stores thickness and velocity values for various materials, as will be described in greater detail later. Signal generator 414 generates an electrical driving signal 436 for wave generating component 416. Wave generating component 416 generates a Lamb wave 438 for receiving component 418. Wave generating component 416 may be any type of electromechanical transducer that is operable to create mechanical energy from electrical energy, a non-limiting example of which includes a piezoelectric device. Parameter estimating component 410 uses time estimating component 420 and attenuation estimating component 422 to estimate a time delay value, $\tau$, and an attenuation value, $\alpha$, for Lamb wave 438, as will be described in greater detail later. Thickness estimating component 412 estimates the thickness of material 402, as will be described in greater detail later.

Controlling component 406 instructs and controls each component of device 400 via control lines 424, 430, 432, 434, 426 and 428. Memory component 408 is controlled via control line 424. Signal generator 414 is instructed and controlled, via control line 430. Wave generating component 416 controlled via control line 432. Receiving component 418 controlled via control line 434. Parameter estimating component 410 is controlled via control line 426. Thickness estimating component 412 is controlled via control line 428.

A method of using a structural health monitoring system to estimate the thickness of a material in accordance with aspects of the present invention will be described in more detail with additional reference to FIG. 5.

Figure 5:
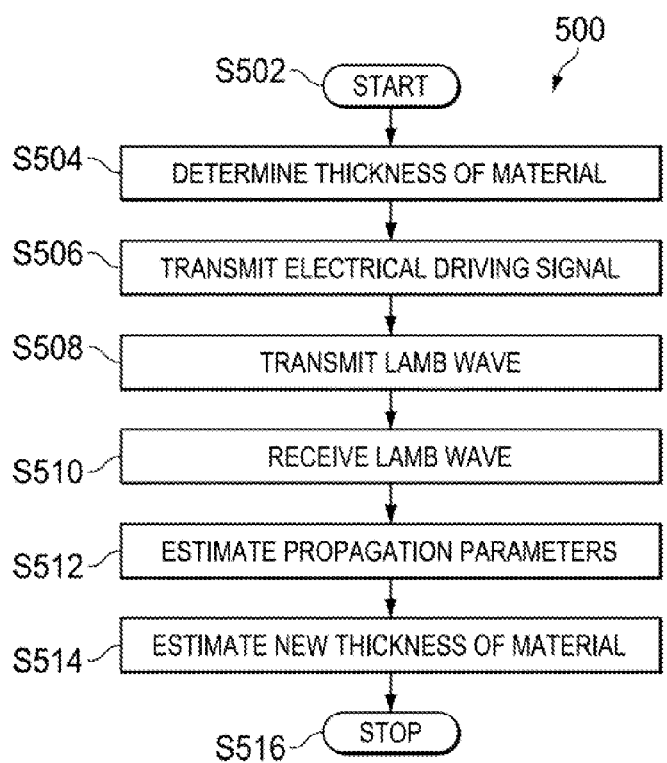
FIG. 5 illustrates an example method of estimating the thickness of a material, in accordance with aspects of the present invention.

FIG. 5 illustrates an example method 500 of estimating the thickness of a material.

Method 500 starts (S502) and the thickness of a material is determined (S504). For example, with reference to FIG. 4, memory component 408 may have the initial thickness of various materials, including the initial thickness of material 402, stored therein. For example, in a first use, the thickness of material 402 may have been factor set within memory component 408. Otherwise, the thickness of material 402 may have been stored in memory component 408 from a previous performance of method 500, as will be explained in greater detail below.

Returning to FIG. 5, an electrical driving signal is then transmitted (S506). For example, with reference to FIG. 4, signal generator 414 generates an electrical driving signal 436 for wave generating component 416. This will now be described in more detail in FIG. 6.

Figure 6:
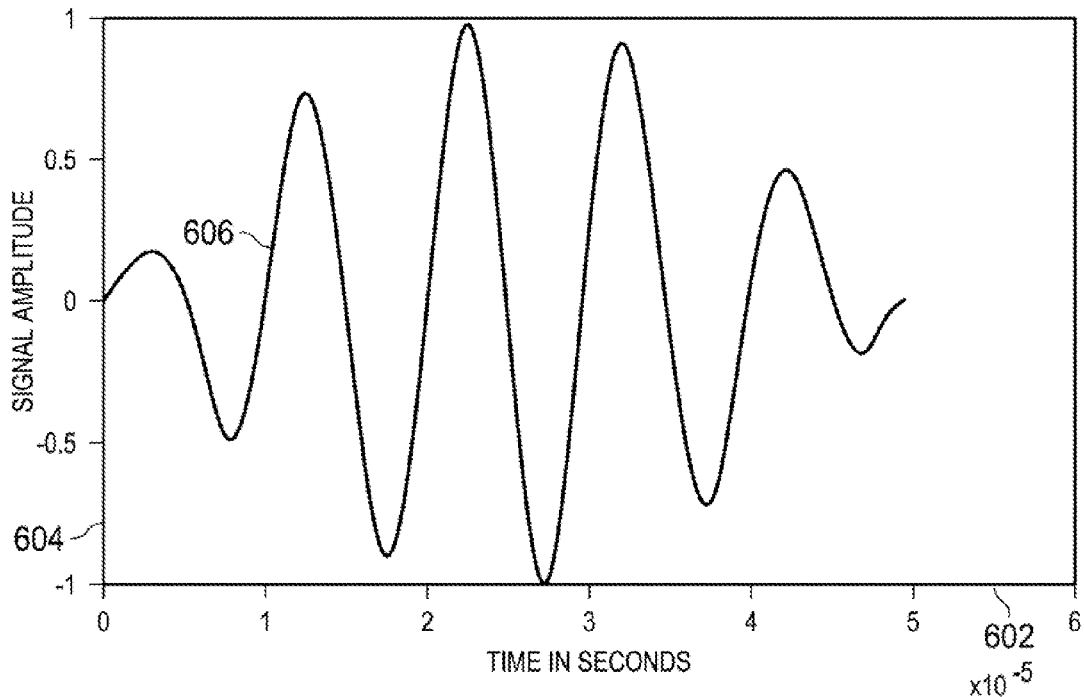
FIG. 6 illustrates a graph of an example electrical driving signal, in accordance with aspects of the present invention.

FIG. 6 illustrates a graph 600 of an example electrical driving signal in accordance with aspects of the present invention.

As shown in FIG. 6, graph 600 includes an x-axis 602, a y-axis 604 and an input signal 606.

Input signal 606 is an example of electrical driving signal 436 that may be generated by signal generator 414. Electrical driving signals of various amplitudes may be used for transmission from a signal generator to a wave generating component and is not limited to the example in FIG. 6.

Returning to FIG. 5, a Lamb wave is then transmitted (S508). For example, with reference to FIG. 4, electrical driving signal 436 from signal generator 414 is transformed into a mechanical signal by wave generating component 416 in order to create a Lamb wave for propagation toward receiving component 418. As wave generating component 416 creates a Lamb wave, wave generating component 416 additionally provides the time of the Lamb wave generation, $t_g$, to controlling portion 406 via control line 432.

Figure 1:
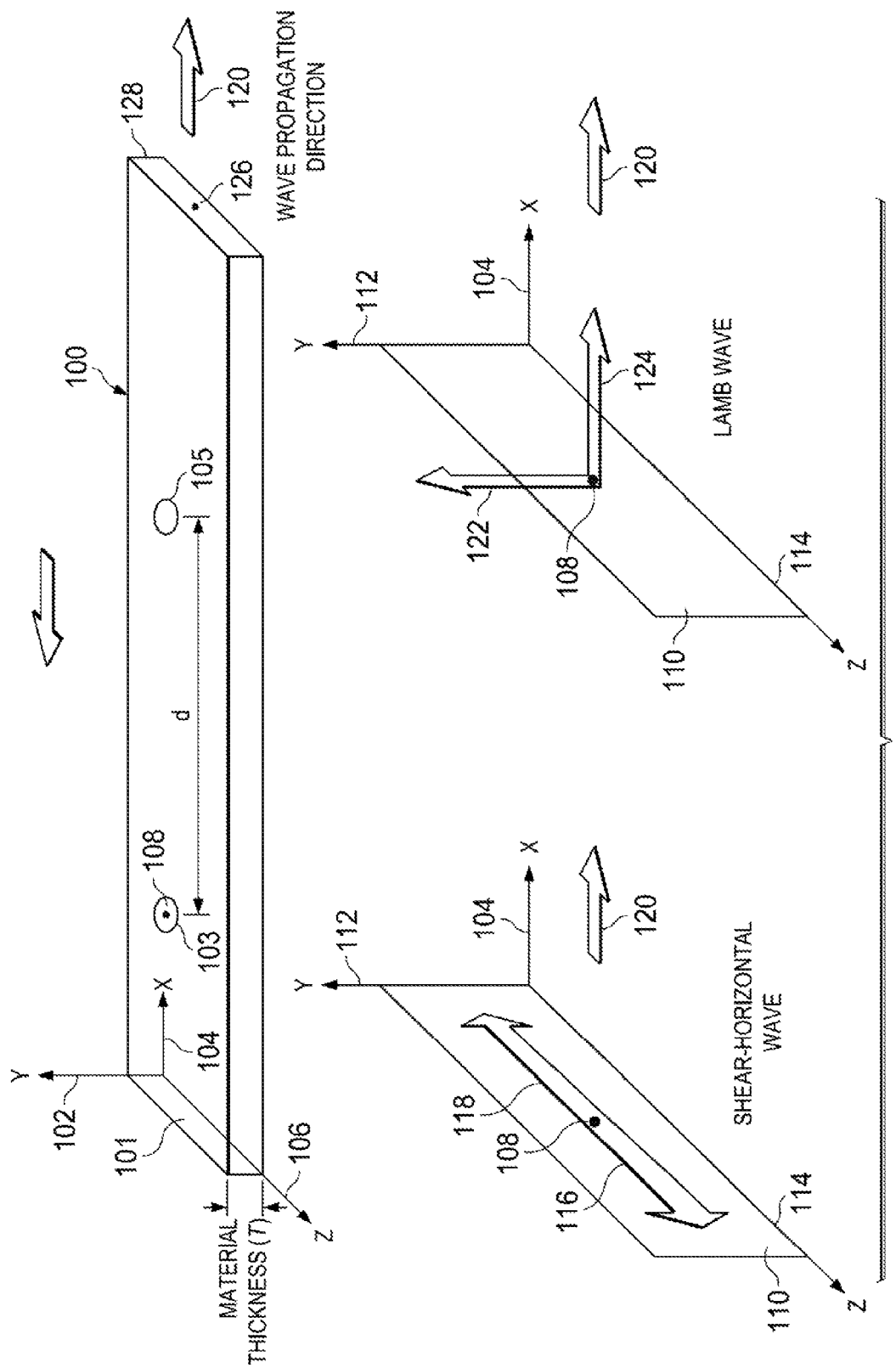
FIG. 1 illustrates propagation of waves through a material.

Consider, for example, with reference to FIG. 1, that wave generating component 416 is disposed at the same position as wave generating component 103, and receiving component 418 is disposed at the same position as receiving component 105. In this case, wave generating component 416 is separated from receiving component 418 by distance d.

Returning to FIG. 5, after the lamb wave is transmitted (S508), it is received (S510). For example, returning to FIG. 4, receiving component 418 is operable to detect the Lamb wave and transform the mechanical enemy of the Lamb wave into an electrical signal. The electrical signal and the time of receipt, $t_r$, of the lamb wave is then provided to controlling component 406 via control line 434.

Figure 2:
FIG. 2 illustrates a view of plane of the material of FIG. 1.

Returning to FIG. 2, after the Lamb wave is received (S510), propagation parameters are estimated (S512). For example, returning to FIG. 4, at this point, controlling component 406 instructs signal generator 414 to generate a specific electrical driving signal.

In some embodiments, the specific frequency of the driving signal is predetermined. In some embodiments, signal generator 414 is operable to generate one of many signals, wherein a user may select a specific signal to be generated. The user may select a specific signal by any known system or mechanism, non-limiting examples of which include a graphic user interface, a keyboard, a dial, etc.

Signal generator 414 provides electrical driving signal 436 to wave generating component 416. Wave generating component generates Lam wave 438. Upon receipt of Lam wave 438, receiving component provides controlling component with the received signal s(t). It should be noted, that there will be a received signal for every mode supported by electrical driving signal 436.

As discussed above with reference to FIG. 3, a material may support many different modes of Lamb waves for any one particular frequency. However, these modes within a specific frequency may travel at different velocities. Further, Lamb waves in different modes have different transmission parameters. In accordance with aspects of the present invention, the different modes of Lamb waves within a specific frequency are distinguished based on their distinct velocity. Once distinguished, the corresponding parameters of each of the different modes of the Lamb are analyzed to estimate a thickness of the material. This will be described in greater detail with reference to FIGS. 7-8.

FIG. 7 illustrates graph 300, with the addition of sampled points 702, 704, 706 and 708.

At low frequencies, only a few modes may be supported. For example, at about 0.1 MHz, only mode 306 and mode 316 are supported as evidenced by sampling point 702 and sampling point 706. Further, at about 0.25 MHz, only mode 306 and mode 316 are supported as evidenced by sampling point 704 and sampling point 708. In other words, returning to FIG. 4, if d is known, and $t_p$ is measured, then a velocity of the propagated Lamb wave may be determined from equation (1) discussed above.

FIG. 8 illustrates a graph 800 of distance versus time for various Lamb waves.

As shown in FIG. 8, graph 800 includes an x-axis 802, a y-axis 804, a line 806, a line 808, a line 810, a point 812, a point 814, a point 816, a point 818, a point 820, a point 822, a point 824, a point 826, and a point 828.

X-axis 802 is time and is measured in microseconds. Y-axis 804 is distance and is measure in cm. In this situation, three receiving components, similar in function to receiving component 418, were used. A first one was positioned 10 cm from wave generating component 416. A second one was positioned 22 cm from wave generating component 416. A third one was positioned 33 cm from wave generating component 416.

Line 806 corresponds to a 100 KHz electrical driving signal from signal generator 414. Lines 808 and 810 correspond to a 215 KHz driving signal from signal generator 414.

In the case of the 100 KHz electrical driving signal, the first receiving component detected a wave at 70 μs after wave generating component 416 generated the Lamb wave, as evidenced by sampling point 812. The second receiving component then detected a wave at 110 μs after wave generating component 416 generated the Lamb wave, as evidenced by sampling point 814. The third receiving component then detected a wave at 150 μs after wave generating component 416 generated the Lamb wave, as evidenced by sampling point 814.

Using linear interpolation of sampling points 812, 814 and 816, the velocity of the Lamb wave associated with the 100 kHz electrical driving signal was derived as line 806. This velocity corresponds to sample point 702 of FIG. 7, thus indicating that the Lam wave corresponded to function 306, which corresponds to the first anti-symmetric mode.

In the case of the 250 KHz electrical driving signal, the first receiving component detected a wave at 40 μs after wave generating component 416 generated the Lamb wave, as evidenced by sampling point 818. The first receiving component then detected a wave at 58 μs after wave generating component 416 generated the Lamb wave, as evidenced by sampling point 820. The second receiving component then detected a wave at 68 μs after wave generating component 416 generated the Lamb wave, as evidenced by sampling point 822. The third receiving component then detected a wave at 86 μs after wave generating component 416 generated the Lamb wave, as evidenced by sampling point 824. The second receiving component then detected a wave at 97 μs after wave generating component 416 generated the Lamb wave, as evidenced by sampling point 826. The third receiving component then detected a wave at 130 μs after wave generating component 416 generated the Lamb wave, as evidenced by sampling point 828.

Using linear interpolation of sampling points 820, 826 and 828, the velocity of a first Lam wave associated with the 250 kHz electrical driving signal was derived as line 808. This velocity corresponds to sample point 704 of FIG. 7, thus indicating that the Lamb wave corresponded to function 306, which corresponds to the first anti-symmetric mode. Further, using linear interpolation of sampling points 818, 822 and 824, the velocity of a second Lam wave associated with the 350 kHz electrical driving signal was derived as line 808. This velocity corresponds to sample point 708 of FIG. 7, thus indicating that the Lam wave corresponded to function 316, which corresponds to the first symmetric mode.

Returning to FIG. 5, after a Lamb wave is received (S510), the propagation parameters are then estimated (S512). For example, with reference to FIG. 4, Lamb wave 438 has propagation parameters associated with it Parameter estimating component 410 estimates this propagation parameter using time estimating component 420 and attenuation estimating component 422.

Returning to FIG. 4, lamb wave 438 is the received, signal, r(t), is a distance, d, from wave generating component 416. In accordance with aspects of the present invention, r(t) is modeled according to the following equation:

$$r(t) = \sum_{i=1}^{n} a_i s_i(t-\tau) + n(t), \quad (2)$$

where s(t) is electrical driving signal 436; modes 1, 2, ..., n propagate in material 402; $s_i(t)$ is the received signal, only from the dispersion of mode i; $\alpha_i$ is the amplitude of the received mode i signal; τ is a constant delay associated with each mode, due to wave generating component 416; and n(t) is Gaussian noise in the measurement.

The amplitudes, $\alpha_i$, and time delay, τ, may be estimated by taking the mean square error (MSE) of the detected Lamb wave 438 from the modeled Lamb wave from equation (2) as follows:

$$MSE(\tau) = \left[ r(t) - \sum_{i=1}^{n} a_i s_i(t-\tau) \right]^2. \quad (3)$$

For example, controlling component 406 provides parameter estimating component 410 with $s_i(t)$, which controlling component 406 had received from receiving component 418. Attenuation estimating component 422 estimates the amplitudes, $\alpha_i$, by minimizing MSE(τ) with the best delay. Similarly, time estimating component 420 estimates the $\alpha_i$ by minimizing the MSE ($\alpha_i$) with the best delay.

There are three unknowns that are estimated by minimizing equation (3) and the equivalent equation for MSE ($\alpha_i$). These unknowns are $\alpha_i$, τ and the thickness of the material. The thickness of the material is based on $s_i(t)$. Although there are three unknowns within one equation each may be determined by known methods, for example by rewriting the equation as three equations using derivatives. For example, the values of x, y and z within a function $f(x,y,z)$ may be determined by rewriting as follows:

$$f(x, dy/dx, dz/dx) = 0 \quad (4)$$

$$f(dx/dy, y, dz/dy) = 0 \text{ and} \quad (5)$$

$$f(dx/dz, dy/dz, z) = 0 \quad (6)$$

Figure 3:
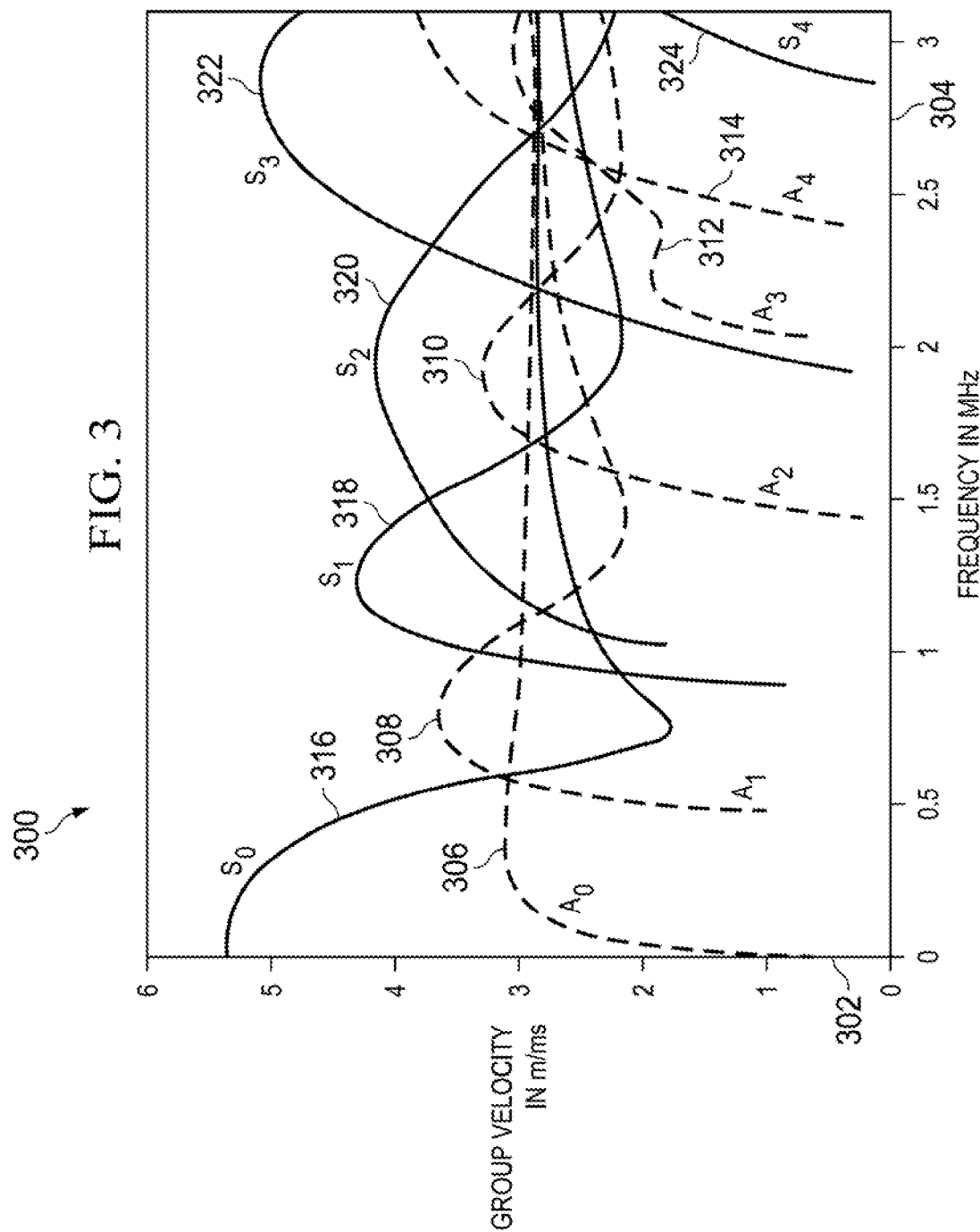
FIG. 3 illustrates a graph of measured frequency versus measured group velocity for different modes of Lamb waves propagated through a 3.18 mm thick aluminum plate.

In the present case, the value for the thickness of the material is within the signal $s_i(t)$. As the thickness changes, the shape of the signal $s_i(t)$ changes, wherein the shape of the signal $s_i(t)$ is based on the dispersion curves, for example as shown in FIG. 3.

In an example embodiment, when choosing values to minimize equation (3), an initial value of the estimated thickness may be used. This initial thickness estimation may be based on a priori information, e.g., a previously measured thickness or thickness as provided by a manufacturer. Using this initial estimated thickness and an estimated $\alpha_i$, the unknown for τ may be calculated in time estimating component 420 by minimizing MSE(τ) with the best delay. Similarly, using this initial estimated, thickness and the calculated τ, the unknown for $\alpha_i$ may be calculated in attenuation estimating component 422 by minimizing MSE ($\alpha_i$) with the best delay. This process is iterated until optimized parameters are calculated.

The computations of equation (3) become more complex as the number of modes increase. In accordance with an aspect of the present invention, it is beneficial to therefore as few modes as possible. For example, returning to FIG. 7, this would include using less than 0.5 MHz for electrical driving signal 436 in the case of a 3.18 mm thick aluminum plate. This is because at 0.5 MHz a third mode, mode 308, is supported and must be accounted for in equation (3).

Returning to FIG. 5, after the propagation parameters have been estimated (S512), new thickness is then estimated (S514). For example, with reference to FIG. 4, thickness estimating component 412 estimates a new thickness of material 402 based on the previously determined time and attenuation estimates.

Returning to FIG. 5, after the new thickness is estimated method 500 then stops (S516).

There are several possible embodiments of the present invention. One embodiment includes a structural health monitoring device that is made along, with the material that is to be analyzed, which was discussed above with reference to FIG. 4. In other embodiments, a structural health monitoring device is made separate from a material that is to be analyzed. This will now be described in more detail in FIGS. 9A-C.

Figure 9A:
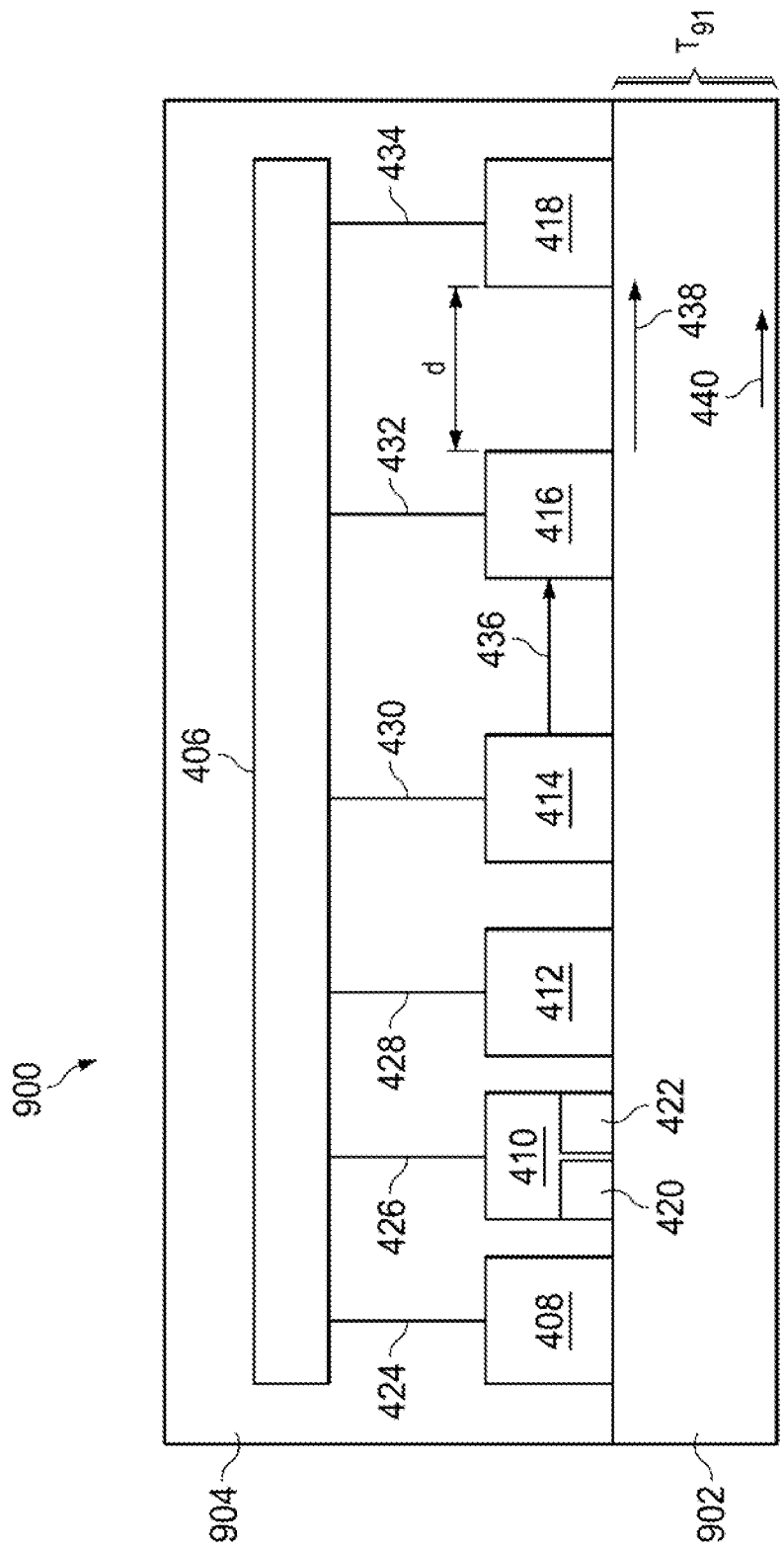

FIG. 9A illustrates an embodiment of a structural health monitoring system 900 in accordance with aspects of the present invention.

As shown in the figure, system 900 includes a monitoring portion 904 and a material 902. Monitoring portion 904 includes controlling component 406, memory component 408, parameter estimating component 410, thickness estimating component 412, signal generator 414, wave generating component 416 and receiving component 418. Parameter estimating component 410 includes time estimating component 420 and attenuation estimating component 422. Monitoring component addition idly includes control line 424, control line 426, control line 428, control line 430, control line 432 and control line 434.

In this embodiment, system 900 differs from device 400 of FIG. 4, in that in system 900, monitoring portion 904 is detachably fastened to material 902, whereas in device 400, monitoring portion 404 is part of not detachable from material 402. Monitoring portion 904 may be detachably fastened to material 902 by any known manner, non-limiting examples of which include fastening devices and adhesives.

For purposes of discussion, suppose that monitoring portion 904 of system 900 is used to determine the thickness. $T_{91}$, of material 902. At that point, monitoring portion 904 may be removed from material 902, as shown in FIG. 9B.

Once removed, monitoring portion 904 may be detachably fastened to another material, as shown in FIG. 9C.

FIG. 9C illustrates an embodiment of a structural health monitoring system 906 in accordance with aspects of the present invention.

As shown in the figure, system 906 includes monitoring portion 904 and a material 908.

For purposes of discussion, suppose that monitoring portion 904 of system 906 is used to determine the thickness, $T_{92}$, of material 908. At that point, monitoring portion 904 may be removed from material 908, as shown in FIG. 9B. In this manner, monitoring portion 904 may be used on many materials.

In accordance with aspects of the present invention, a SHM system and method is used to estimate the thickness of a material. This is done by using the properties associated with Lamb waves to conduct thickness estimations. The system and method, in accordance with aspects of the present invention, is preferred over conventional methods because the device used in the present invention does not require the use of transducers which are precisely placed on the top and bottom surfaces of a material. Rather, the present invention provides a way to accurately convey the thickness of a material by placing the SHM device on top of a material and estimating the thickness by analyzing various properties of transmitted Lamb waves.

The foregoing description of various preferred embodiments of the invention have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A method comprising:
   providing, via a memory component, an initial thickness of a material to be monitored;
   providing, via a signal generator, an electrical driving signal;
   generating, via a wave generating component, a Lamb wave from the electrical driving signal;
   receiving, via a receiving component positioned a predetermined distance from the wave generating component, a received Lamb wave;
   generating, via the receiving component, an electrical received signal based on the received Lamb wave;
   estimating, via a first estimating component, a propagation parameter; and
   estimating, via a thickness estimating component, a new thickness of the material to be monitored based on the initial thickness and the estimated propagation parameter.

2. The method of claim 1, wherein said estimating a propagation parameter comprises estimating a time delay, τ, associated with the wave generating component generating the Lamb wave from the electrical driving signal.

3. The method of claim 2, wherein said estimating a propagation parameter further comprises estimating, via a second estimating component, an attenuation, a, relating the received Lamb wave to the Lamb wave.

4. The method of claim 3, wherein said estimating a new thickness of the material to be monitored comprises estimating the new thickness based on τ and a.

5. The method of claim 2, wherein said estimating a time delay, τ, comprises estimating τ by minimizing a mean square error associated with the electrical received signal.

6. The method of claim 1, wherein said estimating a propagation parameter comprises estimating an attenuation, a, relating the received Lamb wave to the Lamb wave.

7. The method of claim 6, wherein said estimating an attenuation, a, comprises estimating a by minimizing a mean square error associated with the electrical received signal.

8. The method of claim 1, further comprising:
   providing, via the memory component, an initial thickness of a second material to be monitored;
   providing, via the signal generator, a second electrical driving signal;
   generating, via the wave generating component, a second Lamb wave from the second electrical driving signal;
   receiving, via the receiving component positioned a second predetermined distance from the wave generating component, a second received Lamb wave;
   generating, via the receiving component, a second electrical received signal based on the second received Lamb wave;
   estimating, via the first estimating component, a second propagation parameter; and
   estimating, via the thickness estimating component, a new thickness of the second material to be monitored based on the second estimated propagation parameter.

9. A device comprising:
   material having a thickness,
   a memory component operable to provide an initial thickness of said material;
   a signal generator operable to generate an electrical driving signal;
   a wave generating component operable to generate a Lamb wave from the electrical driving signal;

a receiving component, positioned a predetermined distance from the wave generating component, operable to receive a received Lamb wave and to generate an electrical received signal based on the received Lamb wave;

a first estimating component operable to estimate a propagation parameter; and a thickness estimating component operable to estimate a new thickness of said material based on the initial thickness and the estimated propagation parameter.

10. The device of claim 9, wherein said first estimating component comprises a time estimating component operable to estimate a time delay, T, associated with the wave generating component generating the Lamb wave from the electrical driving signal.

11. The device of claim 10, wherein said first estimating component further comprises an attenuation estimating component operable to estimate an attenuation, a, relating the received Lamb wave to the Lamb wave.

12. The device of claim 11, wherein said thickness estimating component is operable to estimate the new thickness of said material to be monitored based on T and a.

13. The device of claim 10, wherein said time estimating component is operable to estimate T by minimizing a mean square error associated with the electrical received signal.

14. The device of claim 9, wherein said first estimating component comprises an attenuation estimating component operable to estimate an attenuation, a, relating the received Lamb wave to the Lamb wave.

15. The device of claim 14, wherein said attenuation estimating component is operable to estimate a by minimizing a mean square error associated with the electrical received signal.

16. A device for use with a material having a thickness, said device comprising:

a memory component operable to provide an initial thickness of the material;

a signal generator operable to generate an electrical driving signal;

a wave generating component operable to generate a Lamb wave from the electrical driving signal;

a receiving component, positioned a predetermined distance from the wave generating component, operable to receive a received Lamb wave and to generate an electrical received signal based on the received Lamb wave;

a first estimating component operable to estimate a propagation parameter; and a thickness estimating component operable to estimate a new thickness of the material based on the initial thickness and the estimated propagation parameter.

17. The device of claim 16, wherein said first estimating component comprises a time estimating component operable to estimate a time delay, T, associated with the wave generating component generating the Lamb wave from the electrical driving signal.

18. The device of claim 17, wherein said first estimating component further comprises an attenuation estimating component operable to estimate an attenuation, a, relating the received Lamb wave to the Lamb wave.

19. The device of claim 18, wherein said thickness estimating component is operable to estimate the new thickness of the material to be monitored based on T and a.

20. The device of claim 17, wherein said time estimating component is operable to estimate T by minimizing a mean square error associated with the electrical received signal.

* * * * *